(12) United States Patent
Cardell et al.

(10) Patent No.: US 7,594,894 B2
(45) Date of Patent: Sep. 29, 2009

(54) ARRANGEMENT FOR ANALYSING RESPIRATORY GASES

(75) Inventors: Mats Cardell, Sollentuna (SE); Peter Svedmyr, Bromma (SE)

(73) Assignee: Artema Medical AB, Sundyberg (SE)

( * ) Notice: Subject to any disclaimer, the term of this patent is extended or adjusted under 35 U.S.C. 154(b) by 287 days.

(21) Appl. No.: 10/593,702

(22) PCT Filed: Mar. 24, 2005

(86) PCT No.: PCT/SE2005/000438

§ 371 (c)(1),
(2), (4) Date: Sep. 20, 2006

(87) PCT Pub. No.: WO2005/094675

PCT Pub. Date: Oct. 13, 2005

(65) Prior Publication Data

US 2008/0091116 A1    Apr. 17, 2008

(30) Foreign Application Priority Data

Mar. 31, 2004 (EP) .................................. 04101330

(51) Int. Cl.
*A61B 5/08* (2006.01)
*G01N 1/22* (2006.01)
(52) U.S. Cl. ........................................ 600/532; 73/23.3
(58) Field of Classification Search ................ 73/24.01, 73/53.01, 23.2, 23.3; 600/529, 532; 422/83, 422/84, 94; 128/203.12, 204.21, 204.22
See application file for complete search history.

(56) References Cited

U.S. PATENT DOCUMENTS

| | | | |
|---|---|---|---|
| 3,927,670 A * | 12/1975 | Turney et al. | 600/532 |
| 5,701,888 A * | 12/1997 | Tham et al. | 128/204.21 |
| 6,076,392 A * | 6/2000 | Drzewiecki | 73/23.2 |
| 6,250,132 B1 * | 6/2001 | Drzewiecki | 73/23.2 |
| 6,272,905 B1 * | 8/2001 | Drzewiecki | 73/53.01 |
| 6,305,212 B1 | 10/2001 | Drzewiecki | |
| 6,896,713 B1 * | 5/2005 | Eckerbom et al. | 55/421 |

(Continued)

FOREIGN PATENT DOCUMENTS

EP    0 823 259 A2    2/1998

(Continued)

OTHER PUBLICATIONS

PCT International Search Report dated Jun. 16, 2005.

(Continued)

*Primary Examiner*—John Fitzgerald
(74) *Attorney, Agent, or Firm*—Kory D. Christensen; Stoel Rives LLP

(57) ABSTRACT

The present invention relates to an arrangement for the analysis of respiratory gases to and from a patient, which is connected to a respirator. The arrangement comprises a holder unit (6) for a removably fitted water trap (4) that is adapted to receive said respiratory gases and the arrangement has a connection that is adapted to lead liquid-free gas from the water trap (4) to an analysing instrument (8). The holder unit is provided with an oxygen gas measuring unit (14) for measuring oxygen gas in the liquid-free gas which is removably attached to said holder unit (6). The present invention also relates to the above mentioned oxygen gas measuring unit (14).

16 Claims, 4 Drawing Sheets

U.S. PATENT DOCUMENTS

Figure 1:
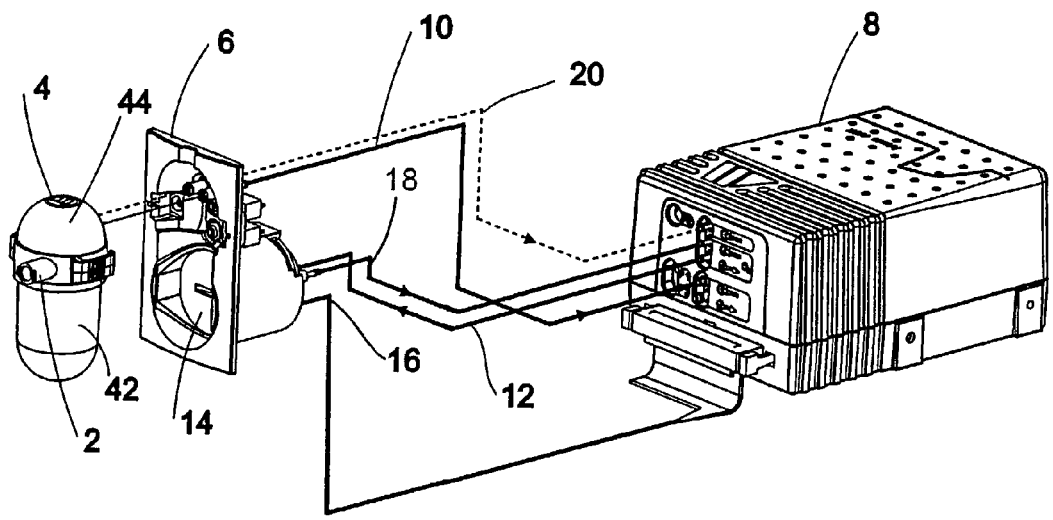

| | | | |
|---|---|---|---|
| 6,981,947 B2* | 1/2006 | Melker | 600/532 |
| 2002/0144937 A1* | 10/2002 | Wilberscheid et al. | 210/85 |
| 2003/0176804 A1* | 9/2003 | Melker | 600/532 |
| 2004/0210152 A1* | 10/2004 | Eckerbom | 600/532 |
| 2007/0167853 A1* | 7/2007 | Melker et al. | 600/532 |
| 2007/0203448 A1* | 8/2007 | Melker et al. | 604/24 |

FOREIGN PATENT DOCUMENTS

| | | |
|---|---|---|
| EP | 0 823 259 A3 | 8/1998 |
| WO | WO 90/04425 A2 | 5/1990 |
| WO | WO 90/04425 A3 | 6/1990 |
| WO | WO 00/45884 A1 | 8/2000 |
| WO | WO 03/017837 A1 | 3/2003 |

OTHER PUBLICATIONS

PCT Written Opinion of the International Searching Authority dated Jun. 16, 2005.

* cited by examiner

ARRANGEMENT FOR ANALYSING RESPIRATORY GASES

This application is a U.S. National Phase Application under 35 USC 371 of International Application PCT/SE2005/000438 filed Mar. 24, 2005.

FIELD OF THE INVENTION

The present invention relates to an arrangement for the analysis of respiratory gases to and from a patient, which patient is connected to a respirator. The arrangement comprises a holder unit for a removably fitted water trap, which holder unit has a connection that leads liquid-free gas from the water trap to an analysing unit. The holder unit is provided with an oxygen gas measuring unit that measures oxygen gas in the respiratory gases, which oxygen gas measuring unit is removably attached to said holder unit.

The present invention also relates to the above mentioned oxygen gas measuring unit.

BACKGROUND OF THE INVENTION

Within the field of respiratory care, for instance in the case of patient anaesthesia, it is often required to measure and monitor a great number of patient gases, such as carbon dioxide, nitrous oxide, oxygen and anaesthesia agents. This is frequently accomplished through so called lateral flow measuring analysers, which take a minor sample flow from the respiratory circuit of a patient to an adjacent instrument comprising a gas analysing unit in which the actual gas analysis takes place. The gas analysing principle is often based on the fact that many gases absorb infrared energy at different wavelengths, i.e. the wavelength absorbed is specific for the substance concerned.

Oxygen gas is however difficult to measure with this principle, since said gas exhibits no marked absorption within the same infra red range as the other gases and also the absorption peak is rather weak in comparison with said other gases. Instead the instrument often comprises a second analysing unit which measures oxygen gas separately. This second analysing unit is often based on the analysing principle which utilizes the paramagnetic properties of oxygen. This kind of unit is however expensive, rather heavy and takes up a lot of space when positioned within the analyzing instrument, where it also is difficult to access. A further drawback is that it is not possible to use a unit that performs measurements based upon the paramagnetic properties of oxygen in combination with magnetic resonance equipment, which generate strong magnetic fields.

Another possibility is to measure oxygen gas with a fuel cell. There are different kinds of fuel cells but generally they comprise an anode and a cathode separated by an electrolyte and produce electric current when supplied with reactants. The reactants are usually hydrogen gas and oxygen gas, supplied at the anode and cathode, respectively, and the electric current produced is directly proportional to the partial pressure of oxygen gas. Within this field it is important that the fuel cell measures the oxygen gas reliably and fast. For instance, a small child has a high breathing frequency, approximately 40-60 breaths per minute, which leads to that the response rise time of the fuel cell needs to be below approximately 0.5 seconds. Fuel cells with a response rise time this low are however consumed rather fast and need to be exchanged approximately once every six to twelve months.

Another issue when measuring expiration gases from a patient is that it is unavoidable that moisture, secretion, blood, bacteria etc., are liable to accompany the sample. Should these substances enter the instrument, there is a potential risk that the instrument will be permanently damaged.

WO 00/45884 discloses a liquid separator that separates liquid from gases, which comprises a water trap removably fitted in a holder unit which is connected to an analysing instrument. The water trap effectively prevents moisture and other harmful substances from entering the analysing instrument.

However, the inventors of the present application have identified a need of an arrangement for the analysis of respiratory gases, which prevents an analysing instrument of being damaged by moisture, that includes an oxygen gas measuring unit, which is less expensive, small and light weight, is easily accessible from the outside of the analysing instrument and that can be used in connection with magnetic resonance equipment.

SUMMARY OF THE INVENTION

Thus, the object of the present invention is to provide an arrangement for the analysis of respiratory gases to and from a patient connected to a respirator. With this arrangement the analysing instrument is prevented from being damaged by moisture and the oxygen gas content in the respiratory gases is measured within an oxygen gas measuring unit which is less expensive, small and light weight, and which is removably fitted and easily accessible from the outside of the analysing instrument. Moreover, said oxygen gas measuring unit is not sensitive for use in connection with magnetic resonance equipment.

These objects are achieved by an arrangement according to the preambles of the independent claims and provided by the features according to the characterising portions of the independent claims.

Preferred embodiments are set forth in the dependent claims.

SHORT DESCRIPTION OF THE DRAWINGS

Figure 2:
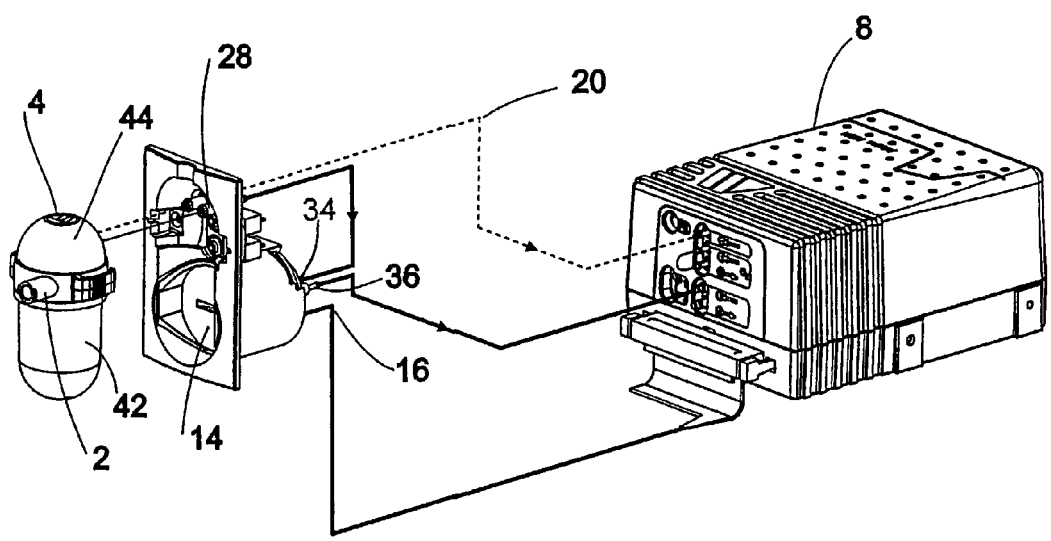
Figure 3:
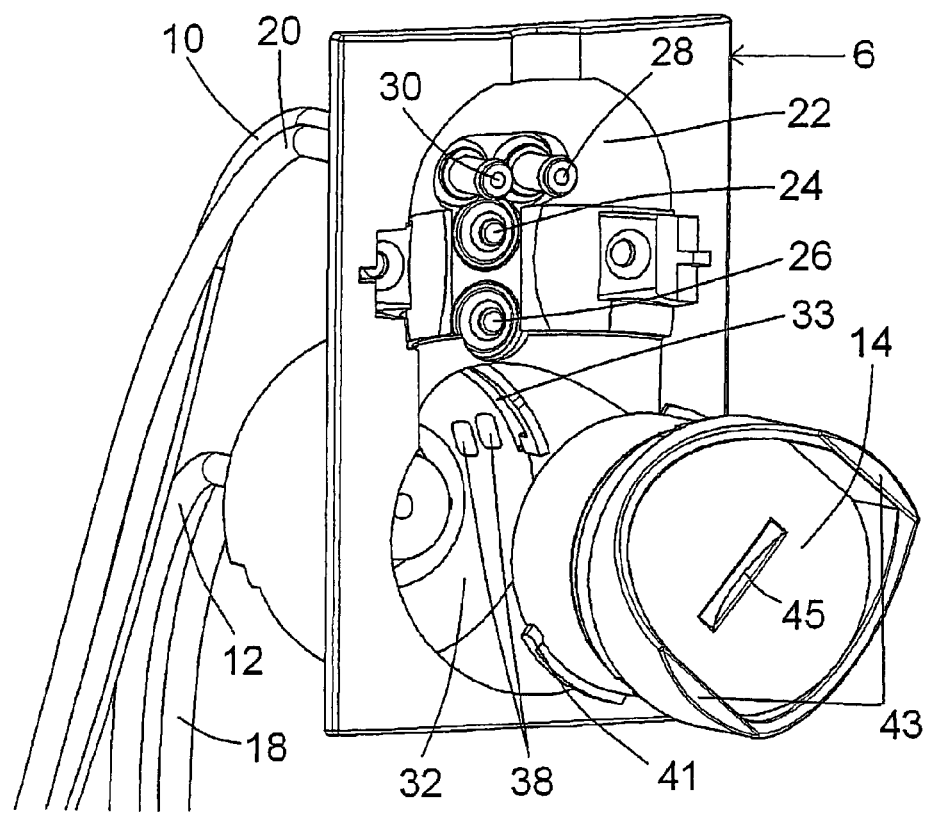
Figure 4:
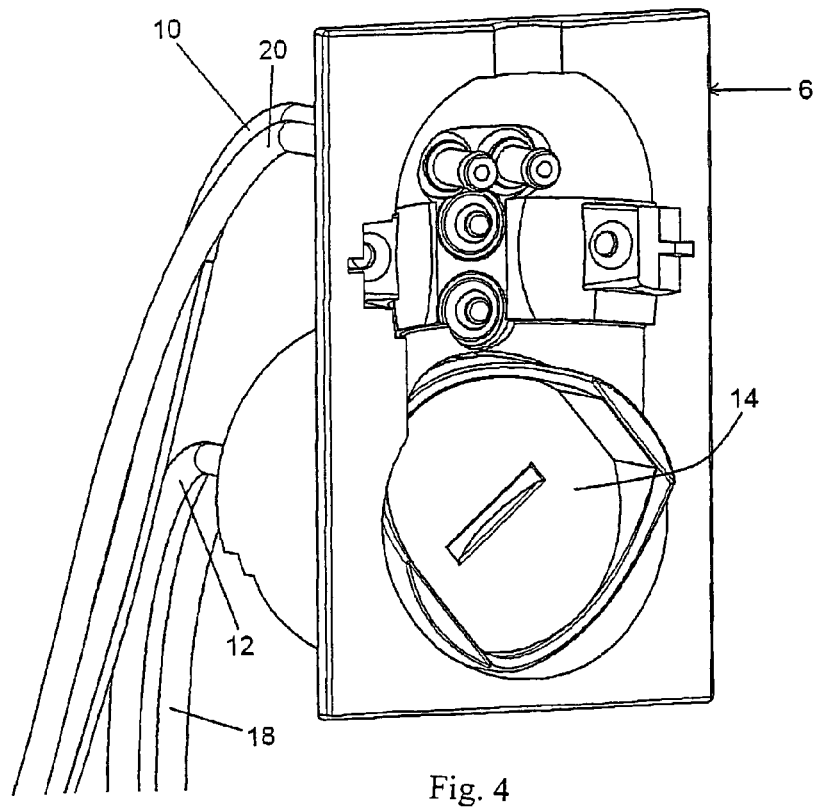
Figure 5:
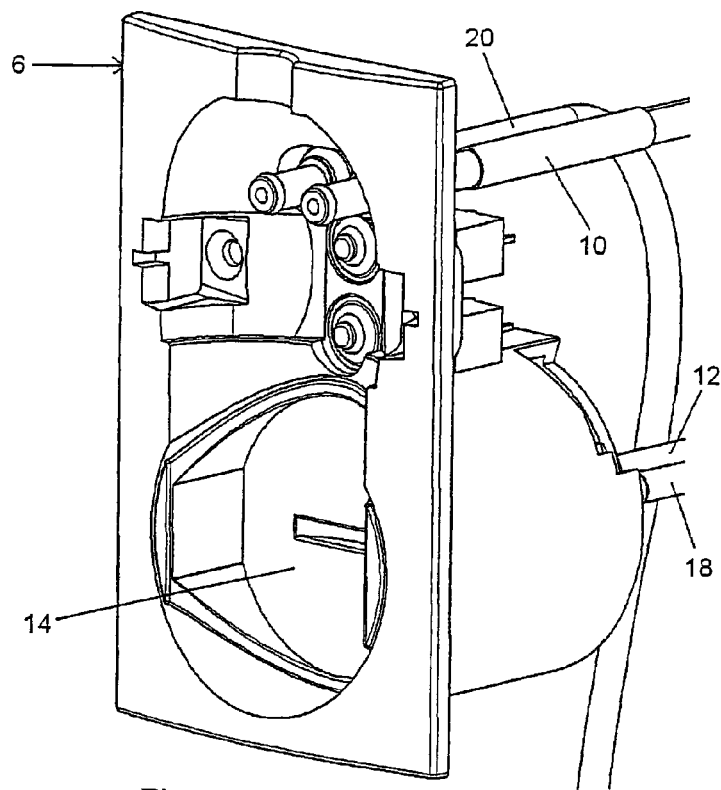
Figure 6:
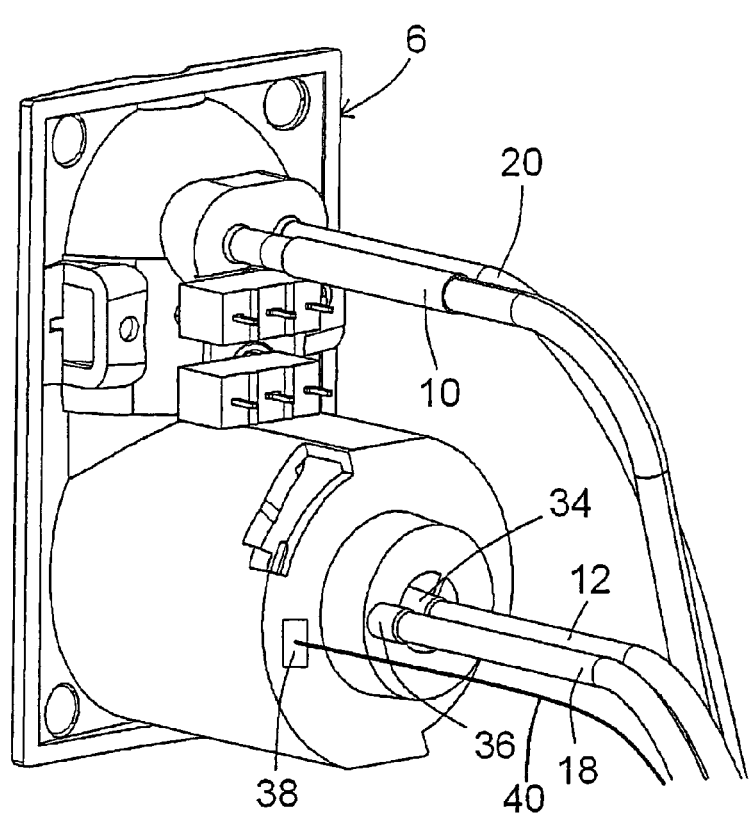
Figure 7:
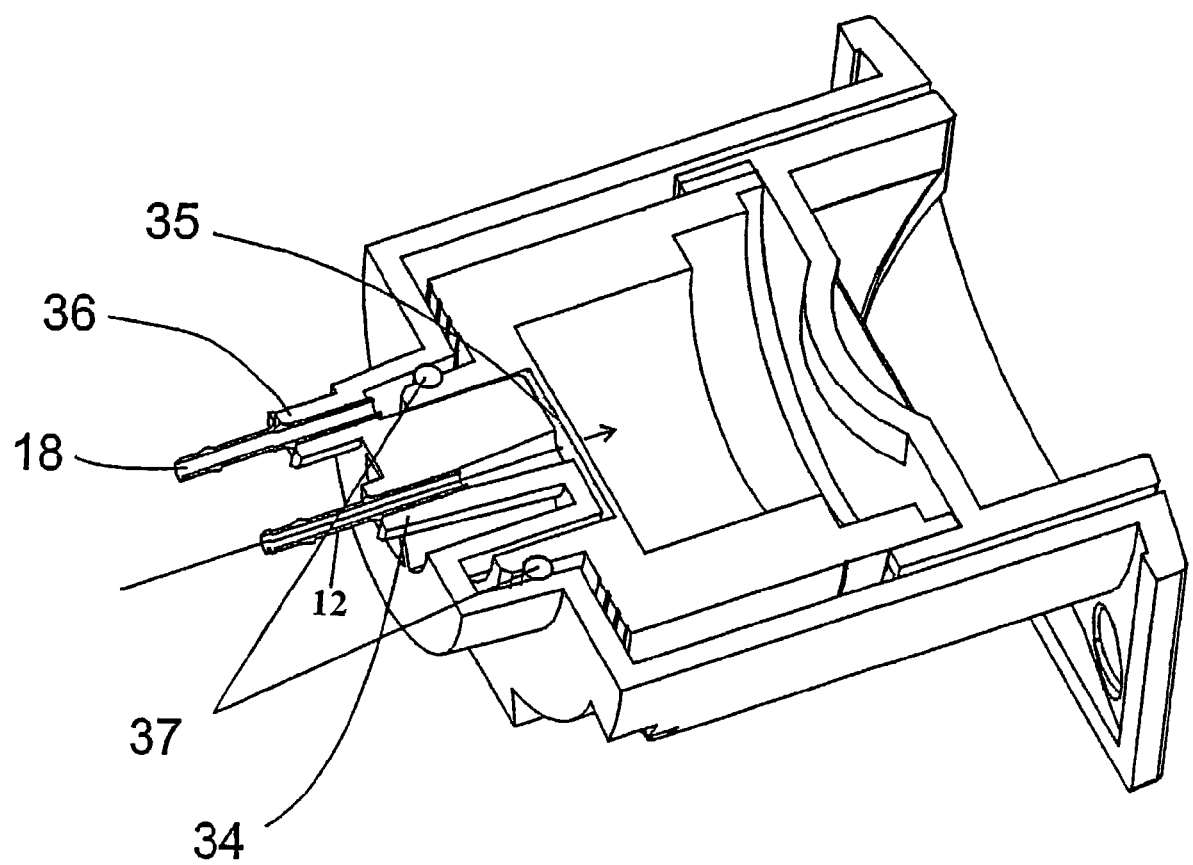

The invention will be described in greater detail below with reference to the attached drawings, in which:

FIG. 1 schematically shows the principal gas flow of a preferred embodiment of the arrangement for analysis of respiratory gases according to the present invention, FIG. 2 schematically shows the principal gas flow of second preferred embodiment of the arrangement for analysis of respiratory gases according to the present invention, FIG. 3 shows, obliquely from the front, a holder unit in the preferred embodiment, with a removable fitted oxygen gas measuring unit in front of the holder unit, FIG. 4 shows, obliquely from the front, the holder unit in the preferred embodiment, with the removable fitted oxygen gas measuring unit inside, FIG. 5 shows, obliquely from the front, the holder unit in the preferred embodiment, with the removable fitted oxygen gas measuring unit inside and in a locked position, and FIG. 6 shows the holder unit in the preferred embodiment from the back, and FIG. 7 shows a horizontal cross section of the holder unit in the preferred embodiment with the fuel cell inside.

DETAILED DESCRIPTION OF THE INVENTION

As seen from FIG. 1, a gas sample is in the preferred embodiment taken from the respiratory circuit of a patient (not shown) who for instance is anaesthetized. The gas sample is led to a connection 2 of a water trap 4 which is removably attached to a holder unit 6, which in turn is connected to an analysing instrument 8. The water trap 4, which will be described in greater detail below as will the holder unit 6, is preferably, but not restricted to, the one disclosed in WO 00/45884, and is adapted to capture and keep the moisture content of the gas sample as well as to prevent bacteria and other unwanted substances to enter the analysing instrument 8. From the water trap 4, the now liquid-free gas sample is led via a first tube 10, connected via the holder unit 6, to a gas analysing unit (not shown) within the analysing instrument 8, which gas analysing unit measures the gas components of the liquid-free gas sample, for instance with infrared technique. Since it is difficult to measure oxygen gas with IR-technique, see discussion above, the liquid-free gas sample is after completion of the measurement led from the gas analysing unit via a second tube 12 back to the holder unit 6 and to an oxygen gas measuring unit 14, removably attached to the holder unit 6. The oxygen gas measuring unit 14 will be described in greater detail below. The oxygen gas measuring unit 14 measures the oxygen gas content of the liquid-free gas sample and transfers information about said content to the analysing instrument 8 via means 16, preferably in the form of electrical signals. The oxygen gas measuring unit 14 may also be adapted to transfer status information of said oxygen gas measuring unit 14 to the analysing instrument 8, preferably via the means 16.

After the oxygen gas measurement, the liquid-free gas sample is led via a third tube 18 from the oxygen gas measuring unit 14, via the holder unit 6, to a pneumatic pump (not shown) within the analysing instrument 8 that controls the flow rate of the gases in the tubing system. Said pump either leads the liquid-free gas sample from the analysing instrument 8 back to the respiratory circuit of the patient (not shown) or to a place (not shown) where it is prevented to adversely affect persons close to the instrument 8, for instance out in the open air. In order to efficiently capture the moisture content of the gas sample before it is led to the analysing instrument 8, the pump is preferably also directly connected to the water trap 4 via a fourth tube 20 and via the holder unit 6, to create an under pressure in the water trap 4. In this instance the fourth tube 20 is preferably provided with a throttle valve (not shown).

As seen from FIG. 3, the holder unit 6 is adapted to house the water trap 4 in an indentation 22 and can be connected to the analysing instrument 8. The holder unit 6 is preferably provided, as also disclosed in WO 00/45884, with electrical contact elements 24, 26 that are adapted to detect the existence and the type of water trap 4 inserted in the holder unit 6, for instance water traps for adults and children respectively. The holder unit 6 is also provided with two connection devices 28, 30 for connecting the first 10 and fourth 20 tube respectively, that lead to the analysing instrument 8, and for connecting gas passageways (not shown) of the water trap 4.

The holder unit 6 is further adapted to house an oxygen gas measuring unit behind the water trap 4, preferably in a second indentation 32 in the lower part of the holder unit 6. In the back of the indentation 32 there are grooves 33 that are adapted to engage corresponding protruding means 41 provided on the oxygen gas measuring unit 14, see below.

The holder unit 6 is provided with connection devices 34 and 36 for connecting the second 12 and third 18 tube respectively, that lead from and to the analysing instrument 8.

Further, the holder unit 6 is provided with means 16 that are adapted to send information about the oxygen gas content in the liquid-free gas sample from the oxygen gas measuring unit 14 to the analysing instrument 8. Said means comprises in the preferred embodiment electrical contact(s) 38 in the back of the second indentation 32, which are connected to the analysing instrument 8 via electrical cable(s) 40. However, said means are not restricted to send information about the oxygen gas content via electrical communication, but said information could for instance be transferred via optical fibres, radio waves or via IR.

The oxygen gas measuring unit 14 is in the preferred embodiment a fuel cell. The fuel cell in use is not restricted to the type of fuel cells described above, but can be any fuel cell that is adapted to measure oxygen gas. It is however provided that the oxygen gas measuring unit 14 is removably attachable to the holder unit 6. For this reason the oxygen gas measuring unit 14 is in the preferred embodiment provided with protruding edges 41 that correspond to the grooves 33, so that when the oxygen gas measuring unit 14 is inserted in to the second indentation 32 of the holder unit 6 with a twisting motion, the grooves 33 engage said edges 41 so that the oxygen gas measuring unit 14 now is in a locked position. The oxygen gas measuring unit 14 is provided with protruding wings 43 in order to be easily inserted with said twisting motion into said second indentation 32. In order to easily remove the oxygen gas measuring unit 14 from its locked position in the holder unit 6, the oxygen gas measuring unit 14 is provided with a notch 45, in which notch 45 a screwdriver or a similar tool can be inserted, in order to facilitate the reverse twisting motion that removes the oxygen gas measuring unit 14 from the locked position. Thereafter, the wings 43 also facilitate the removal of the oxygen gas measuring unit 14. The wings 43 and the notch 45 can naturally have different designs as long as they are adapted to facilitate the insertion and removal of the oxygen gas measuring unit 14 from the holder unit 6.

The insertion and locking of the oxygen gas measuring unit 14 is however not restricted to the preferred method of insertion described above. There are other ways the oxygen gas measuring unit 14 can be removably attached to the holder unit 6. For instance the oxygen gas measuring unit 14 can be provided with protruding pins (not shown) that correspond to holes (not shown) in the back of the second indentation 32. The oxygen gas measuring unit 14 and the second indentation can also be provided with threads (not shown), so that the oxygen gas measuring unit 14 can be screw threaded in to the second indentation 32, or the oxygen gas measuring unit 14 can be provided with for instance an O-ring of proper size (not shown) along its circumferential edge so that the oxygen gas measuring unit 14 can be pushed into and kept inside the second indentation 32 by means of friction.

The oxygen gas measuring unit 14 is provided with means for receiving as well as emitting the liquid-free gas sample from the analysing instrument 8, i.e. a gas passageway that corresponds to and communicates with the connection devices 34 and 36 in the holder unit 6. In the preferred embodiment the liquid-free gas is transported from the analysing instrument 8 through connection device 34, and meets a membrane 35 in the back of the oxygen gas measuring unit 14, through which membrane 35 the liquid-free gas is transported into the oxygen gas measuring unit 14. After measurement of the oxygen gas content, the liquid-free gas is transported through said membrane 35 and out through connection device 36 and back to the analysing instrument 8. With this arrangement the volume of liquid-free gas that enters the oxygen gas measuring unit 14 is minimized, and excess gas is transported to the sides (illustrated with dashed arrows) and subsequently out through connection device 36 and back to the analysing instrument 8. Further there are sealing means 37 provided that prevent leakage of gas.

The oxygen gas measuring unit 14 is also provided with means (not shown) that correspond to the means 16 in the holder unit 6 that are adapted to send information about the oxygen gas content in the liquid-free gas sample from the oxygen gas measuring unit 14 to the analysing instrument 8. Therefore, the means on the oxygen gas measuring unit 14 also preferably comprise electrical contacts that transfer electrical signals with information about the oxygen gas content, and/or status information of the oxygen gas measuring unit 14, from the oxygen gas measuring unit 14, to the electrical contacts 38 in the holder unit 6, and to the analysing instrument 8.

As mentioned above, the water trap 4 is preferably the water trap disclosed in WO 00/45884. As seen from FIG. 1 the water trap 4 is provided with a connection 2 for receiving gas flow from the patient. The water trap 4 includes a container 42, which collects the liquid contained in the gas sample and which is located beneath, and removably attached to, a separation chamber 44, which comprises a liquid passageway (not shown) as well as a filter (not shown) above said liquid passageway, that efficiently collects bacteria and other unwanted substances. Above the separation chamber 44 is an upper part chamber that includes a gas passageway (not shown) that corresponds to the liquid gas passageway in the separation chamber 44 and that leads to two connection gas passageways (not shown), by means of which the water trap 4 can be connected to the connection devices 28, 30 in the holder unit 6. With this connection, a main flow that is transferred from the water trap 4 to the analysing instrument 8 as well as a secondary flow that passes the container 42 is accomplished. Moreover, the holder unit 6 is provided with interlocking means that correspond to interlocking means (not shown) on the water trap 4, by means of witch the water trap 4 can be removably attached to the holder unit 6.

Different gases have different rise times. In the tubing system, every abrupt alteration of area, every curve and bend may cause turbulent flow, thus spreading out the gas wave front adversely affecting said rise times and for this reason, one wishes to measure the content of the gas with the most critical rise time as soon as possible in the tubing system. In this instance, said gas is usually carbon dioxide and therefore the measuring of carbon dioxide, as well as of other gas components of the liquid-free gas sample, not including oxygen gas, takes place first and the measuring of the oxygen content of the gas sample takes place at the end of the tubing system.

However, in second preferred embodiment, see FIG. 2, it is possible to lead the liquid-free gas sample from the water trap 4 directly to the oxygen gas measuring unit 14, preferably from connection device 28 via a short tube to connection device 34. After the measurement, the liquid-free gas sample is transported from the oxygen gas measuring unit 14 via connection device 36 and the third tube 18, which tube leads the liquid-free gas sample to the analysing unit. From the analysing unit, the liquid-free gas sample is after measurement of the other desired gas components, led to the pump and for instance out in the open air or to another place, see discussion above. In this second preferred embodiment, said fourth tube 20 between the pump and the water trap 4 is provided as described above in the preferred embodiment and the information about the oxygen gas content in the liquid-free gas sample is transferred to the analysing unit by any of the ways described above.

It will be understood that the invention is not restricted to the above-described exemplifying embodiments thereof and that several conceivable modifications of the invention are possible within the scope of the following claims.

The invention claimed is:

1. An arrangement for the analysis of respiratory gases provided to and from a patient connected to a respirator, comprising:
a holder unit for a removably fitted water trap that is adapted to receive said respiratory gases, and
a connection that is adapted to provide liquid-free gas from the water trap to an analysing instrument to which analysing instrument the holder unit is connected, wherein
said holder unit includes an oxygen gas measuring unit for measuring oxygen gas in the liquid-free gas,
said oxygen measuring unit receives the liquid-free gas after analysis of the liquid-free gas by the analysing instrument, and
said oxygen gas measuring unit is a fuel cell which is removably attached to said holder unit and has a connection that is adapted to receive the liquid-free gas from the analysing instrument via said holder unit.

2. An arrangement according to claim 1, wherein said arrangement further comprises a connection that is adapted to transport the liquid-free gas to the analysing instrument.

3. An arrangement according to claim 1, wherein said holder unit has a first indentation adapted to house the water trap and a second indentation adapted to house the fuel cell behind the water trap, so that said holder unit holds the fuel cell between the water trap and the analysing instrument.

4. An arrangement according to claim 1, wherein said arrangement further comprises a connection that is adapted to transport the liquid-free gas from the analysing instrument to the fuel cell.

5. An arrangement according to claim 4, wherein said arrangement further comprises a connection that is adapted to transport the liquid-free gas to the analysing instrument.

6. An arrangement according to claim 1, wherein said fuel cell is provided with means adapted to perform signal communication with the analysing instrument and that the signal communication includes information about the oxygen gas content in the liquid-free gas and/or information about the status of the fuel cell.

7. An arrangement according to claim 6, wherein said fuel cell is provided with at least one contact and the holder unit is provided with at least one corresponding contact that enables said signal communication.

8. An arrangement according to claim 7, wherein said holder unit has a first indentation adapted to house the water trap and a second indentation adapted to house the fuel cell behind the water trap, so that said holder unit holds the fuel cell between the water trap and the analysing instrument.

9. An arrangement according to claim 8, wherein said holder unit is provided with interlocking means in the second indentation that correspond to interlocking means on the fuel cell.

10. An arrangement according to claim 9, wherein said interlocking means in the second indentation of the holder unit are at least one groove and that said interlocking means on the fuel cell are at least one protruding edge.

11. A fuel cell adapted to measure oxygen gas in a liquid free gas, the fuel cell being removably attachable to an arrangement for the analysis of respiratory gases provided to and from a patient connected to a respirator, the arrangement comprising a holder unit for a removably fitted water trap that is adapted to receive said respiratory gases, and a connection that is adapted to provide the liquid-free gas from the water trap to an analysing instrument to which analysing instrument the holder unit is connected, wherein said fuel cell is attachable to the holder unit and has a connection that is adapted to receive the liquid-free gas from the analysing instrument after analysis of the liquid-free gas by the analysing instrument.

12. A fuel cell according to claim 11, wherein said fuel cell is provided with interlocking means that correspond to interlocking means in the holder unit.

13. A fuel cell according to claim 12, wherein said interlocking means on the fuel cell comprise at least one protruding edge that corresponds to at least one groove in the holder unit.

14. A fuel cell according to claim 11, wherein said fuel cell has a connection that is adapted to receive gas and/or a connection that is adapted to emit gas.

15. A fuel cell according to claim 14, wherein said fuel cell is provided with means adapted to perform signal communication.

16. A fuel cell according to claim 15, wherein said fuel cell is provided with at least one contact that corresponds with at least one contact in the holder unit that enables said signal communication.

* * * * *